(12) United States Patent
Kashimura et al.

(10) Patent No.: US 11,286,615 B2
(45) Date of Patent: Mar. 29, 2022

(54) CABLE AND MEDICAL HOLLOW TUBE

(71) Applicant: Hitachi Metals, Ltd., Tokyo (JP)

(72) Inventors: Seiichi Kashimura, Tokyo (JP);
Masamichi Kishi, Tokyo (JP);
Takanobu Watanabe, Tokyo (JP);
Kimika Kudo, Tokyo (JP); Masashi Arai, Tokyo (JP)

(73) Assignee: HITACHI METALS, LTD., Tokyo (JP)

( * ) Notice: Subject to any disclaimer, the term of this patent is extended or adjusted under 35 U.S.C. 154(b) by 394 days.

(21) Appl. No.: 16/411,709

(22) Filed: May 14, 2019

(65) Prior Publication Data

US 2019/0352848 A1 Nov. 21, 2019

(30) Foreign Application Priority Data

May 17, 2018 (JP) .............................. JP2018-095112
Aug. 31, 2018 (JP) .............................. JP2018-162773
Apr. 24, 2019 (JP) .............................. JP2019-082944

(51) Int. Cl.
*D07B 5/00* (2006.01)
*A61L 29/04* (2006.01)
(Continued)

(52) U.S. Cl.
CPC ............ *D07B 5/006* (2015.07); *A61L 29/042* (2013.01); *A61L 29/085* (2013.01); *A61L 29/126* (2013.01); *A61L 29/14* (2013.01); *A61M 25/0045* (2013.01); *D07B 1/16* (2013.01); *A61B 2562/222* (2013.01); *A61L 2420/02* (2013.01); *A61L 2420/08* (2013.01);
*D07B 2201/2087* (2013.01); *D07B 2201/2088* (2013.01); *D07B 2201/2092* (2013.01); *D07B 2205/2082* (2013.01); *D07B 2501/2084* (2013.01); *D07B 2801/18* (2013.01)

(58) Field of Classification Search
None
See application file for complete search history.

(56) References Cited

U.S. PATENT DOCUMENTS 4,232,081 A * 11/1980 Pullan ................... B60J 10/24
428/122
5,358,786 A 10/1994 Ishikawa et al.
(Continued)

FOREIGN PATENT DOCUMENTS

CN 1681554 A 10/2005
CN 104927454 B 3/2017
(Continued)

OTHER PUBLICATIONS

Innovation Q plus IP.com—PG pub (Year: 2021).*
(Continued)

*Primary Examiner* — Peter A Salamon
(74) *Attorney, Agent, or Firm* — Roberts Calderon Safran & Cole P.C.

(57) ABSTRACT

A cable includes a sheath, and a coating film covering a circumference of the sheath. The coating film adheres to the sheath. The static friction coefficient of a surface of the coating film is smaller than the static friction coefficient of a surface of the sheath. The adhesion strength between the sheath and the coating film is 0.30 MPa or more.

12 Claims, 6 Drawing Sheets

(51) Int. Cl.
*A61L 29/08* (2006.01)
*A61L 29/12* (2006.01)
*A61L 29/14* (2006.01)
*D07B 1/16* (2006.01)
*A61M 25/00* (2006.01)

(56) References Cited

U.S. PATENT DOCUMENTS

| | | | |
|---|---|---|---|
| 5,521,009 | A | 5/1996 | Ishikawa et al. |
| 8,162,855 | B2 | 4/2012 | Sakane et al. |
| 8,192,373 | B2 | 6/2012 | Sakane et al. |
| 10,258,765 | B2 | 4/2019 | Kashimura et al. |
| 2006/0073264 | A1 | 4/2006 | Sakane et al. |
| 2006/0286139 | A1 | 12/2006 | Ai-Lamee |
| 2007/0224509 | A1* | 9/2007 | Aramata .............. H01M 4/136 429/231.95 |
| 2007/0299402 | A1 | 12/2007 | Ishii et al. |
| 2011/0177230 | A1 | 7/2011 | Sakane et al. |
| 2018/0036509 | A1* | 2/2018 | Kashimura .......... A61L 29/085 |
| 2019/0352848 | A1* | 11/2019 | Kashimura .............. D07B 1/16 |
| 2021/0079258 | A1* | 3/2021 | Kashimura .............. C09D 7/69 |

FOREIGN PATENT DOCUMENTS

| | | |
|---|---|---|
| CN | 1076800724 A | 2/2018 |
| JP | 5-12924 A | 1/1993 |
| JP | 2008-000287 A | 1/2008 |
| JP | 2012-007289 A | 1/2012 |
| JP | 2018-23758 A | 2/2018 |

OTHER PUBLICATIONS

Shin-Etsu, X-52-1621 TDS (Year: 2021).*
Office Action issued in the corresponding Japanese Patent Application No. 2019-082944 dated Jul. 23, 2019.
Extended European Search Report issued in the corresponding EP Application No. 20168371.1 dated Aug. 17, 2020.
Extended European Search Report issued in the corresponding EP Application No. 19174807.8 dated Oct. 14, 2019.
Office Action issued in the corresponding Chinese Patent Application No. 2019104131334 dated Sep. 18, 2021.
Office Action issued in the corresponding Korean Patent Application No. 10-2019-0055988 dated Sep. 8, 2021.

* cited by examiner

R: REACTIVE GROUP (ex. METHYL GROUP)

SOFT ◄─────────────────► HARD

LIGHT ◄─────────────────► HEAVY

20: SHEATH
21: PARENT MATERIAL
22: FINE PARTICLES

CABLE AND MEDICAL HOLLOW TUBE

CROSS-REFERENCE TO RELATED APPLICATION

The present application is based on Japanese patent application No. 2018-95112 filed on May 17, 2018, Japanese patent application No. 2018-162773 filed on Aug. 31, 2018, and Japanese patent application No. 2019-82944 filed on Apr. 24, 2019, the entire contents of which are incorporated herein by reference.

BACKGROUND OF THE INVENTION

1. Field of the Invention

The present invention relates to a cable and a hollow tube for medical use, and to a technique effective in applying to, for example a probe cable connectable to a medical device or a hollow tube such as a tube into which a catheter is inserted.

2. Description of the Related Art

JP-A-2008-287 describes a technique relating to a medical coating composition capable of imparting stable slidability without applying a lubricant to a surface.

SUMMARY OF THE INVENTION

The surface of the cable is formed with a sheath thereover made of an insulating member. It is desired that this sheath has no stickiness and the like and has a good sliding property (slidability). On the other hand, an end portion of the cable is processed in such a manner as to attach a protective member such as a boot to the sheath with an adhesive. Here, in the cable to which the protective member is attached, for example, when the end portion of the cable is bent, a coating film formed over the surface of the sheath peels off, and the protective member may come off the cable. That is, the cable is required to have no stickiness over the surface of the cable, to have a good sliding property, and to be formed with the coating film over the surface of the sheath being unlikely to peel off.

The cable in one embodiment comprises a sheath and a coating film covering a circumference of the sheath and adhering to the sheath. At this time, a static friction coefficient of the surface of the coating film is smaller than a static friction coefficient of the surface of the sheath, and an adhesion strength between the sheath and the coating film is 0.30 MPa or more.

The hollow tube for medical use according to one embodiment includes a hollow tube body and a coating film covering at least one of an inner surface and an outer surface of the hollow tube body and adhering to the hollow tube body. At this time, a static friction coefficient of the surface of the coating film is smaller than a static friction coefficient of the surface of the hollow tube body, and an adhesion strength between the hollow tube body and the coating film is 0.30 MPa or more.

Points of the Invention

According to one embodiment, it is possible to provide the cable which has no stickiness over the surface of the cable, has a good sliding property, and which is formed with the coating film over the surface of the sheath being unlikely to peel off.

According to one embodiment, it is possible to provide the hollow tube for medical use which has no stickiness over the surface of the hollow tube, has a good sliding property and which is formed with the coating film over the surface of the hollow tube body being unlikely to peel off.

DETAILED DESCRIPTION OF THE PREFERRED EMBODIMENTS

In all the drawings for explaining the embodiments, the same members are denoted by the same reference numerals in principle, and the repetitive descriptions thereof will be omitted. Note that even in a plan view, hatching may be added to make the drawings easy to understand.

<Review of Improvement>

For example, in cables used for medical applications, importance is placed on handling of probes in inspection. Specifically, polyvinyl chloride (PVC) is used for the sheath of the cable, but as the use period becomes longer, a phenomenon such as discoloration occurs in the sheath made of the PVC. From this fact, it is considered that silicone rubber excellent in heat resistance and chemical resistance is used as the sheath particularly for cables used for medical applications.

However, the sheath made of silicone rubber has a sticky nature (so-called "tack", "tackiness", or the like), the sliding property (slidability) is not excellent. Therefore, when the silicone rubber is applied to the sheath of the cable, there arises the problem that it is easy for the cable to be caught in other members, and that dust is also easy to adhere to the surface of the cable. In particular, when the cable is easily caught in other members, for a probe cable connected to a medical device (e.g., an ultrasonic imaging device), handling of the cable becomes difficult. This is because, in the ultrasonic imaging device for example, since inspection is performed while moving the ultrasonic probe connected to the probe cable on the human body, the probe cable is easily caught in the cables or in clothes or the like and it becomes impossible to move the ultrasonic probe smoothly. Therefore, in cables used for medical applications, it is desired that the cable does not have the tack and that the surface of the cable has a good sliding property (slidability).

Regarding this point, in order to realize a highly slidable cable with the reduced tack of the surface, it is necessary to reduce the frictional resistance of the surface of the cable, and as means for reducing the frictional resistance of the surface of the cable, it has been studied that a coating film with a low static friction coefficient is formed over the surface of the sheath. However, according to the study of the present inventor, it is found that when the coating film having a low static friction coefficient is formed over the surface of the sheath, new room for improvement becomes obvious.

For example, a boot as a protective member is attached to an end portion of the cable. In this case, the coating film formed over the outermost surface of the cable and the boot are attached together with an adhesive. However, according to the studies of the present inventors, when the coating film covering the sheath is formed in order to improve the sliding property of the cable, the adhesion strength between the sheath and the coating film becomes small, and as a result, when bending pressure is applied to the boot attached to the cable, peeling occurs at the interface between the sheath and the coating film, and the boot comes off the cable. In other words, when the coating film with a small static friction coefficient is formed over the surface of the sheath in order to improve the sliding property of the surface of the cable, the adhesion strength between the sheath and the coating film is smaller than the bonding strength between the sheath and the boot. As a result, the boot comes off the cable. Therefore, the present embodiment is devised to suppress the boot from detaching from the cable while forming the coating film having a small static friction coefficient over the surface of the sheath. Hereinafter, the technical idea of this embodiment devised will be described.

<Structure of Cable>

In this embodiment, as one example of the cable, a probe cable connectable to a medical device will be described.

Figure 1A:
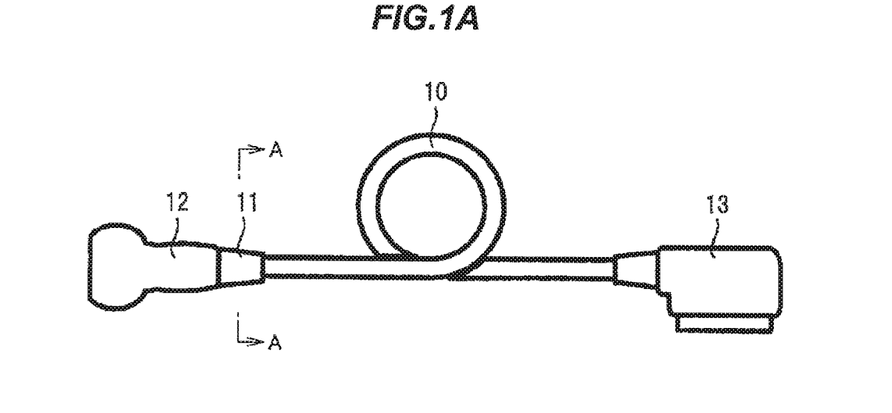
FIG. 1A is a schematic diagram showing a probe cable connectable to an ultrasonic imaging device.
Figure 1B:
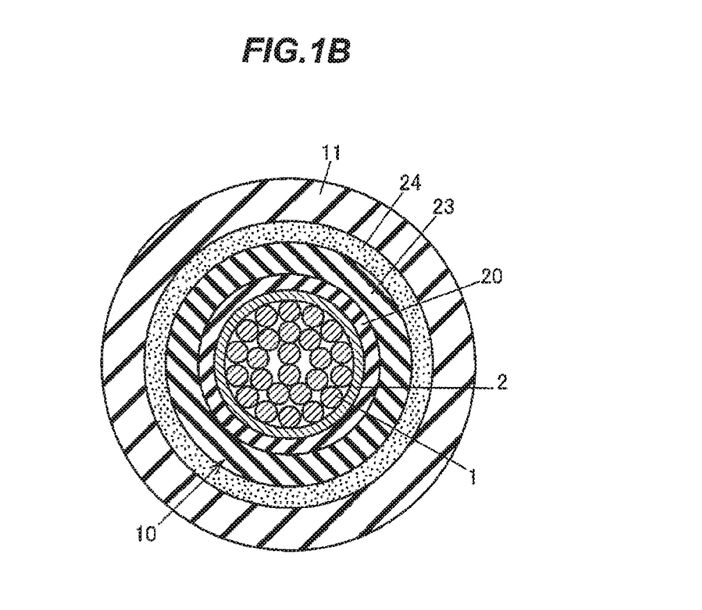
FIG. 1B is a cross sectional view of the probe cable along A-A line.

FIG. 1A is a schematic diagram showing a probe cable 10 connectable to an ultrasonic imaging device. In FIG. 1A, an ultrasonic probe terminal 12 to be connected to an ultrasonic probe is attached to one end portion of the probe cable 10 via a boot 11 for protecting this one end portion. On the other hand, a connector 13 to be connected to the main body of the ultrasonic imaging device is attached to the other end portion of the probe cable 10. FIG. 1B is a cross sectional view of the probe cable 10 along A-A line. For example, a plurality oaf coaxial cables 1 are accommodated inside the probe cable 10 configured as described above, and a shield 2 is provided so as to cover the plurality of coaxial cables (electric wires) 1. A sheath 20 made of an insulating protective member is then provided so as to cover the shield 2. Furthermore, in the probe cable 10 according to the present embodiment, a coating film 23 that covers the above-described sheath 20 and that adheres to the sheath 20 is formed. Further, a boot 11 is attached to the probe cable 10 as a protective member for ann end portion of the probe cable 10, via an adhesive 24 provided around the coating film 23. It should be noted that, in the present embodiment, silicone-based adhesive is used as the adhesive 24, but the present invention is not limited thereto and epoxy-based adhesive and the like may be used.

The sheath 20 is made of, e.g., silicone rubber. On the other hand, in this embodiment, the coating film covering the sheath 20 is configured to include, e.g., silicone rubber or chloroprene rubber. In particular, the coating film is configured to include a parent material and fine particles dispersed in the parent material. Giving one specific example, the coating film includes a parent material made of silicone rubber, and the fine particles dispersed in the parent material include any one of silicone resin fine particles, silicone rubber fine particles, or silica fine particles. Of course, plural kinds may be mixed. It is preferable that the above-mentioned fine particles have hardness higher than that of the parent material (e.g., hardness of on the order of 1.1 times or more in Shore (durometer A) hardness). Note that in the case of silicone rubber fine particles, it may be a spherical powder called so-called silicone composite powder in which the surface of a spherical silicone rubber powder is coated with a silicone resin.

Here, the average particle diameter of the fine particles contained in the coating film is, e.g., 1 μm or more and 10 μm or less. The thickness of the coating film is then, e.g., 3 μm or more and 100 μm or less. In this manner, the probe cable according to the present embodiment is configured.

<Producing Method of Cable>

Next a producing method of the probe cable according to the present embodiment will be described. First, for example, after an electric wire typified by a coaxial cable is formed, a plurality (e.g., 100 or more) of the electric wires are bundled together. Then, a shield is formed so as to cover the bundled plural electric wires (shield forming step). For example, the shield is composed of a braided shield. The braided shield is a shield formed by braiding several conductors together and crossing copper wires. Subsequently, a sheath made of, e.g., silicone rubber is formed so as to cover the shield (sheath forming step). This sheath can be formed, e.g., by extruding silicone rubber using an extruder. Thereafter, in the present embodiment, a coating film which covers the circumference of the sheath and which adheres to the sheath is formed (coating film formation step). This coating film can be formed by, e.g., a dipping method, a spray coating method, a roll coating method, or the like. At this time, the dipping method is a technique of forming a coating film over the surface of the sheath by pulling up the probe cable forming the sheath through the liquid covering material. This dipping method is superior to the spray coating method and the roll coating method in that the film thickness of the coating film formed over the surface of the sheath can be formed uniformly. That is, from the viewpoint of improving the film thickness uniformity of the coating film formed over the surface of the sheath, it is preferable to use the dipping method as the method of forming the coating film.

In this embodiment, for example, since the coating film is composed of the parent material and the fine particles dispersed in the parent material, the liquid covering material used in the dipping method contains the fine particles. At this time, the proportion of the fine particles contained in the coating film is determined by appropriately adjusting the proportion of the fine particles contained in the liquid covering material. In particular, it is desirable that the weight percentage of the fine particles contained in the coating film is 10 mass % or more and 60 mass % or less by adjusting the proportion of the fine particles contained in the liquid covering material.

Characteristics in Embodiment

<<Features>>

Next, a feature of the present embodiment will be described. The feature of this embodiment is that the coating film having its surface having a static friction coefficient smaller than the static friction coefficient of the surface of the sheath is formed over the surface of the sheath in order to suppress stickiness of the surface of the sheath made of silicone rubber. As a result, it is possible to inhibit the probe cable from being caught due to the stickiness of the surface of the sheath, thereby improving the handleability of the probe cable. In the present embodiment, the coating film having the following constitution is then formed over the surface of the sheath, thereby realizing the coating film having its surface having a static friction coefficient smaller than the static friction coefficient of the surface of the sheath. This point will be explained below.

Figure 2:
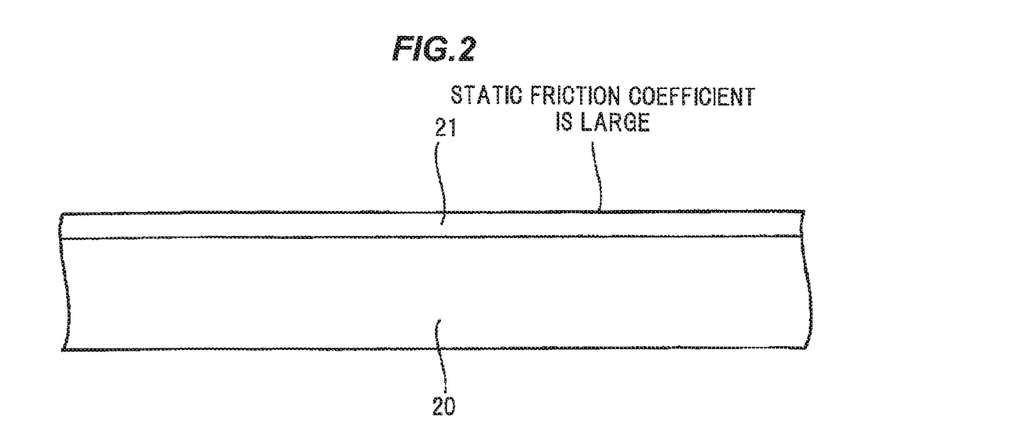
FIG. 2 is a diagram showing a configuration example in which a coating film is formed over a surface of a sheath.

FIG. 2 is a diagram showing a configuration example in which the coating film is formed over the surface of the sheath 20. The coating film shown in FIG. 2 is composed of a parent material 21. In this case, since the surface of the coating film (parent material 21) in FIG. 2 is flat (even), the contact area between the coating film and the contact material in contact with the probe cable is equivalent to the contact area between the sheath 20 and the contact object in the case where the surface of the sheath 20 is exposed without forming the coating film. This means that static friction coefficient of the coating shown in FIG. 2 is equivalent to static friction coefficient of the sheath 20, and it is impossible to realize the constitution "to form the coating film having the surface with a static friction coefficient smaller than the static friction coefficient of the surface of the sheath 20" that is the feature point in this embodiment. That is to say, it is not possible to form the coating film having a static friction coefficient smaller than that of the surface of the sheath 20 merely by forming the coating film made of the parent material 21 so as to cover the surface of the sheath 20. Therefore, the present embodiment is devised to realize the coating film having the surface with the static friction coefficient smaller than the static friction coefficient of the surface of the sheath 20.

Figure 3:
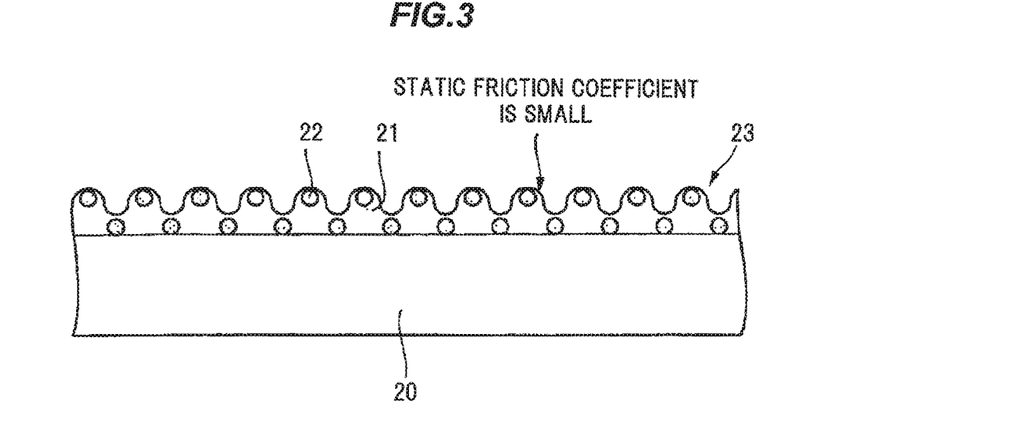
FIG. 3 is a diagram showing a schematic configuration of a coating film in an embodiment.

FIG. 3 is a diagram showing a schematic configuration of the coating film in this embodiment. In FIG. 3, the coating film is formed over the surface of the sheath 20 of the probe cable. This coating film is composed of a parent material 21 and fine particles 22 dispersed in the parent material 21. Since the coating film according to the present embodiment thus constituted contains a plurality of the fine particles 22, as shown in FIG. 3, an uneven shape due to the presence of the fine particles 22 is formed over the surface of the coating film. In this case, due to the uneven shape of the surface, the contact area between the coating film and the contact material contacting the probe cable is smaller than that of the coating film composed of the parent material 21 shown in FIG. 2. This means that static friction coefficient of the coating film in which the fine particles 22 are dispersed in the parent material 21 shown in FIG. 3 is smaller than static friction coefficient of only the parent material 21 shown in FIG. 2. As a result, according to the coating film of the present embodiment, it is possible to form the coating film having the surface with a static friction coefficient smaller than the static friction coefficient of the surface of the sheath 20. In other words, the roughness of the uneven shape of the surface of the coating film is larger than the roughness of the uneven shape of the surface of the sheath 20. In this manner, according to the probe cable having the coating film in this embodiment, it is possible to suppress the catching of the probe cable due to the stickiness of the surface of the sheath 20. Thus, according to the first feature point in the present embodiment, the handleability of the probe cable can be improved.

Next, the materials constituting the coating film in this embodiment will be described. The coating film in this embodiment is composed of a parent material 21 and fine particles 22 dispersed in the parent material 21. At this time, the parent material 21 of the coating film is made of, e.g., silicone rubber. On the other hand, the fine particles 22 dispersed in the parent material 21 are configured to include any one of silicone rubber fine particles, silicone resin fine particles, or silica fine particles.

Figure 4:
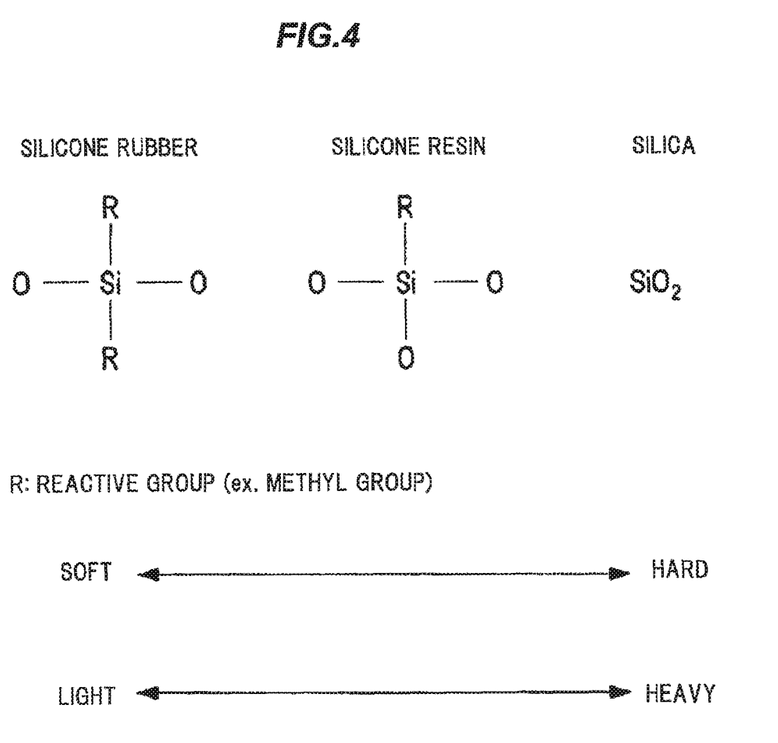
FIG. 4 is a diagram for explaining the difference between silicone rubber, silicone resin, and silica.

Here, differences between silicone rubber, silicone resin and silica will be described. FIG. 4 is a diagram for explaining the differences between silicone rubber, silicone resin, and silica. In FIG. 4, the main difference between the silicone rubber and the silicone resin is the number of reactive groups (e.g., methyl groups) contained in the structural formula. As shown in FIG. 4, the number of reactive groups contained in the structural formula of the silicone rubber is larger than the number of reactive groups contained in the structural formula of the silicone resin. On the other hand, the silica contains no reactive group, and the silica is so-called silicon oxide. Here, as shown in FIG. 4, when the number of reactive groups is large, it has soft characteristics, whereas as the number of reactive groups decreases, it has hard characteristics. The hardness is increased in the order of the silicone rubber, silicone resin, and silica. On the other hand, the mass is increased in the order of the silicone rubber, silicone resin, and silica. Here, from the viewpoint of maintaining the uneven shape formed over the surface of the coating film 23, the silica having high hardness is most desirable, and the silicone resin is desirable as the second best. This is because when the contacting object comes into contact with the uneven shape of the coating film 23, the more the fine particles 22 have the hard characteristic, the higher the effect of suppressing the easy deformation of the fine particles 22 due to the pressing pressure from the contacting material. Therefore, it becomes easy to prevent the uneven shape of the surface of the coating film 23 caused by the fine particles 22 from gentle relaxation. That is, it is possible to prevent static friction coefficient of the surface of the coating film 23 from becoming large due to the gentle relaxation of the uneven shape formed over the surface of the coating film 23 and the increase of the contact area between the coating film 23 and the contact object.

As described above, the silica has the property of being heavier than the silicone rubber and silicone resin. For example, in the dipping method described in <Cable Producing Method>, it is necessary to uniformly disperse the fine particles 22 in the liquid silicone rubber as a material of the parent material, but due to the heavy weight of silica itself, it is sometimes easy to sediment without diffusing uniformly into the liquid silicone rubber as compared with the silicone rubber or the silicone resin lighter than the silica. Therefore, from the viewpoint of uniformly dispersing the fine particles 22 in the coating film 23, fine particles composed of the silicone rubber or silicone resin are more desirable than fine particles made of the silica.

From the above, in order to both maintain the uneven shape formed over the surface of the coating film 23 and make the static friction coefficient of the surface of the coating film 23 small and to disperse the fine particles 22 uniformly in the parent material, the silicone resin is most desirable as the fine particles 22.

<<Novel Findings>>

Next, findings newly discovered by the inventors will be described. The feature of the first embodiment described above is that the coating film 23 having its surface with a static friction coefficient smaller than the static friction coefficient of the surface of the sheath 20 is formed. As a result, in the probe cable 10 according to the present embodiment, the coating film 23 is formed so as to cover the surface of the sheath 20. This inevitably means that there is an interface between the sheath 20 and the coating film 23. Then, due to the existence of the interface between the sheath 20 and the coating film 23, the adhesion strength at the interface between the sheath 20 and the coating film 23 becomes manifest as a problem.

For example, a terminal is attached to the end portion of the probe cable 10, but in order to protect this terminal, a protective member called a boot 11 is attached to the end portion of the probe cable 10. In this case, the probe cable 10 and the boot 11 are bonded together with an adhesive. For example, in a probe cable 10 over which no coating film is formed, the sheath 20 and the boot 11 are bonded together with an adhesive. On the other hand, in the probe cable 10 according to the present embodiment, as a result of the coating film 23 covering the surface of the sheath 20 being formed, the coating film 23 and the boot 11 are bonded together with an adhesive. At this time, according to the investigation by the present inventors, it has newly been found out that the adhesion strength between the sheath 20 and the coating film 23 becomes smaller than the bonding strength between the sheath 20 and the boot 11 in the absence of the coating film, so it becomes apparent that the boot 11 is detached from the probe cable 10.

Figure 5:
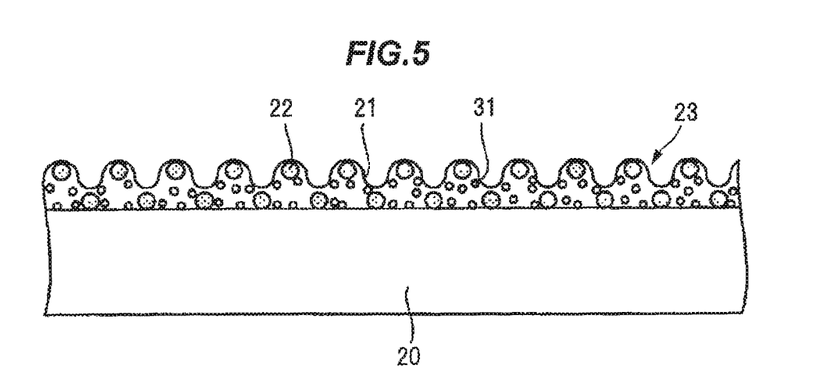
FIG. 5 is a schematic diagram showing that the density of the voids in the silicone rubber constituting the parent material of the coating film is larger than the density of the voids in the silicone rubber constituting the sheath.

Regarding this point, as a result of intensive investigation by the present inventors on the cause of the adhesion strength at the interface between the sheath 20 and the coating film 23 being smaller than the bonding strength between the coating film 23 and the boot 11, it has been found that the adhesion strength at the interface between the sheath 20 and the coating film 23 is weakened by the following mechanism. That is, the parent material 21 constituting the coating film 23 is composed of the silicone rubber, but as a result of investigation by the present inventors, for the condensation reaction type silicone rubber coating agent which is generally commonly used, when the silicone rubber is solidified from the liquefied silicone rubber, the gas escapes from the silicone rubber, whereby voids are formed in the solidified silicone rubber. For example, FIG. 5 is a schematic diagram showing that voids 31 are generated in the silicone rubber constituting the parent material 21 of the coating film 23. As shown in FIG. 5, as the density of the voids 31 in the silicone rubber constituting the parent material 21 of the coating film 23 increases, many voids 31 also exist at the interface between the coating film 23 using the silicone rubber as the parent material 21 and the sheath 20. This means that the presence of the voids 31 reduces the contact area at the interface between the coating film 23 and the sheath 20. As a result, the adhesion strength at the interface between the coating film 23 and the sheath 20 is considered to be small.

Figure 6:
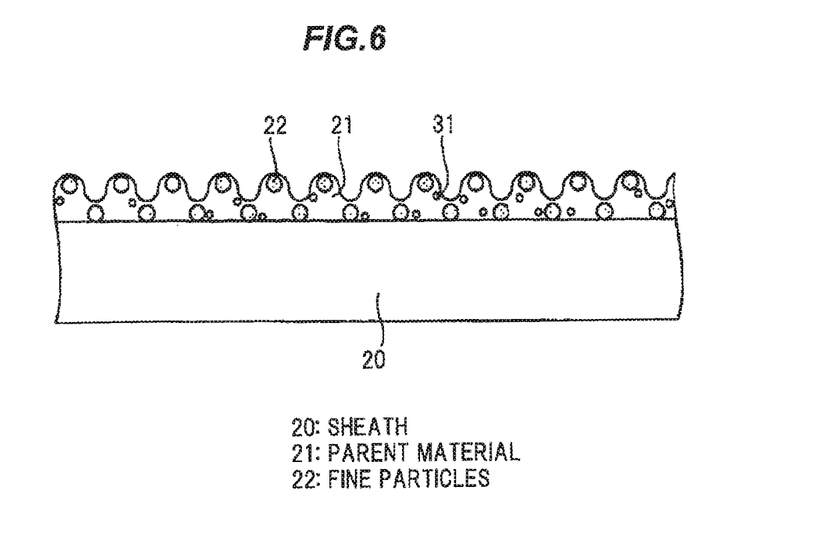
FIG. 6 is a schematic diagram showing that the density of the voids in the silicone rubber constituting the parent material of the coating film is equal to the density of the voids in the silicone rubber constituting the sheath.

Then in the probe cable using the condensation reaction type silicone rubber coating agent, it has been inferred that since the coating film 23 has the voids 31, the adhesion strength between the sheath 20 and the coating film 23 decreases, and when the bending pressure is applied to the boot 11 attached to the probe cable 10, peeling occurs at the interface between the sheath 20 and the coating film 23 before peeling of the bonded portion of the coating film 23 and the boot 11, and the boot 11 is detached from the probe cable 10. Therefore, it is important to reduce the void density in the silicone rubber constituting the parent material 21 of the coating film 23 to improve the adhesion strength between the sheath 20 and the coating film 23. Specifically, as shown in FIG. 6, when the void density in the silicone rubber constituting the parent material 21 of the coating film 23 decreases, the voids 31 existing at the interface between the coating film 23 using the silicone rubber as the parent material 21 and the sheath 20 decrease. This means that the decrease in the contact area at the interface between the coating film 23 and the sheath 20 is suppressed by the reduction of the voids 31. As a result, it is considered that the adhesion strength at the interface between the coating film 23 and the sheath 20 can be improved.

In other words, the finding newly discovered by the present inventors is that if the void density in the silicone rubber constituting the parent material of the coating film 23 can be reduced, the adhesion strength between the sheath 20 and the coating film 23 can be made larger than the bonding strength between the coating film 23 and the boot 11.

<<Summary>>

From the above, according to the present embodiment described above, it is possible to prevent the boot 11 from detaching from the probe cable 10 while forming the coating film 23 having its surface with a smaller static friction coefficient than that of the surface of the sheath 20. That is, according to the probe cable 10 of the present embodiment, it is possible to improve handling of the probe cable 10 and improve reliability of the probe cable 10 at the same time. In particular, the feature of the present embodiment resides in that the coating film 23 having its surface having a static friction coefficient smaller than a static friction coefficient of the surface of the sheath 20 is formed, and by this feature point, the probe cable 10 having a static friction coefficient of the surface of the coating film 23 of 0.5 or less is realized. In addition, the configuration is realized in which the adhesion strength between the sheath 20 and the coating film 23 is equal to the bonding strength between the coating film 23 and the boot 11, or greater than the bonding strength between the coating film 23 and the boot 11. Specifically, according to the feature points in this embodiment, the probe cable 10 having adhesion strength between the sheath 20 and the coating film 23 of 0.30 MPa or more is realized.

<Technical Significance of the Numerical Range>

Next, the technical significance of the numerical range will be explained. First, the average particle diameter of the fine particles 22 contained in the coating film 23 is desirably 1 µm or more and 10 µm or less. It should be noted that "average particle diameter" (average particle size) herein means the average particle diameter measured by laser diffraction method. At this time, when the value is less than the lower limit "1 µm" of the average particle diameter of the fine particles, the uneven shape formed over the surface of the coating film 23 becomes gentle, resulting in a large static friction coefficient of the surface of the coating film 23, and the surface stickiness of the probe cable 10 cannot be eliminated. On the other hand, if it exceeds "10 µm" which is the upper limit value of the average particle diameter of the fine particles 22, as the mass of the fine particles increases, the fine particles 22 sediment, resulting in coating unevenness when applying a coating film material to the surface of the sheath by the dipping method. Therefore, from the viewpoint of suppressing the coating unevenness of the fine particles 22 contained in the coating film 23 while ensuring the small static friction coefficient of the surface of the coating film 23, it is desirable that the average particle diameter of the fine particles 22 contained in the coating film 23 is 1 µm or more and 10 µm or less.

Next, the content of the fine particles 22 contained in the coating film 23 is desirably not less than 10% by mass and not more than 60% by mass. At this time, when the content of the fine particles 22 is less than the lower limit "10% by mass", the number of the fine particles 22 becomes too small and the uneven shape formed over the surface of the coating film 23 cannot be roughened. As a result, static friction coefficient of the surface of the coating film becomes large, and the stickiness of the surface of the probe cable cannot be eliminated. On the other hand, when the content of the fine particles 22 exceeds "60 mass %" which is the upper limit value, the coating film 23 becomes brittle. Therefore, from the viewpoint of suppressing the brittleness of the coating film 23 while ensuring the small static friction coefficient of the surface of the coating film 23, the content of the fine particles contained in the coating film is desirably not less than 10% by mass and not more than 60% by mass.

Subsequently, the thickness of the coating film 23 is desirably 3 µm or more and 100 µm or less. The "thickness of the coating film" herein is a thickness of an entire coating film 23 after forming the coating film 23 containing the fine particles 22. The average particle diameter of the fine particles 22 is appropriately selected in accordance with the thickness of the coating film 23. At this time, the reason for defining the thickness of the coating film to be "3 µm" or more is that it is considered that even if the surface of the probe cable is wiped off 10,000 times, the coating film does not disappear. For example, a probe cable used for a medical device may become soiled by adhesion of blood or the like. In view of frequent wiping off of stains adhering to the surface of the probe cable, it is also desired that the wiping resistance is excellent. On the other hand, the reason why the thickness of the coating film is set at "100 µm" or less is that it is considered that not only the producing cost will increase but also that the flexibility and the bending property will be deteriorated if the thickness of the coating film 23 is too thick. The average particle diameter of the fine particles to be added to the coating film 23 is selected to be equal to or less than the thickness of the coating film 23.

<Verification of Advantageous Effects>

A test probe cable was produced and evaluated in the following manner. A cable produced by twisting 200 coaxial cables having a diameter of about 0.25 mm was covered with a braided wire, which was used as a cable core, and a sheath material was extrusion coated at the rate of 5 m/min around the outer circumference thereof with an extruder. Silicone rubber (static friction coefficient: 1.0 or more) was used as the sheath material. Here, as a material of the silicone rubber, KE-541-U manufactured by Shin-Etsu Chemical Co., Ltd. was used. Other than this type, addition curable (reaction type) silicone rubbers such as KE-551-U, KE-561-U, KE-571-U, and KE-581-U (all of them are manufactured by Shin-Etsu Chemical Co., Ltd.) and the like may be used.

After covering the sheath, the surface of the sheath was cleaned, and then a silicone rubber coating film was formed over the sheath surface to produce a cable of Example 1. As the silicone rubber coating agent, a coating solution was produced, by selecting an addition reaction type material in which byproducts were produced by a curing reaction and had no volumetric shrinkage. Specifically, 120 parts by mass of silicone resin fine particles having an average particle diameter of 2 µm (trade name: KMP-590, manufactured by Shin-Etsu Chemical Co., Ltd.), 600 parts by mass of toluene as a viscosity adjusting solvent, 8 parts by mass of a curing inhibitor (trade name: CAT™, manufactured by Shin-Etsu Chemical Co., Ltd.) and 0.3 parts by mass of a curing catalyst (trade name: CAT-PL-2, manufactured by Shin-Etsu Chemical Co., Ltd.) were added to 100 parts by mass of an addition reaction type silicone rubber coating agent (trade name: SILMARK™, produced by Shin-Etsu Chemical Co., Ltd.) to produce a solution in which the proportion of the silicone resin fine particles to the coating film was 54.5% by mass. Next, using this solution, a silicone rubber coating film was formed over the surface of the sheath by a dip coating method (lifting rate: 2 m/s). Thereafter, drying and curing treatment was carried out at a temperature of 150 degrees C. for 10 minutes. The film thickness of the produced silicone rubber coating film was about 17 µm. Note that the content of the silicone resin fine particles in the above coating film was calculated assuming that the coating agent hardened substantially without mass loss (approximately equal to the blending mass ratio).

Next, as Example 2, 150 parts by mass of silicone resin fine particles having an average particle diameter of 2 µm (trade name: KMP-590, manufactured by Shin-Etsu Chemical Co., Ltd.), 600 parts by mass of toluene as a viscosity adjusting solvent, 8 parts by mass of a curing inhibitor (trade name: CAT™, manufactured by Shin-Etsu Chemical Co., Ltd.) and 0.3 parts by mass of a curing catalyst (trade name: CAT-PL-2, manufactured by Shin-Etsu Chemical Co., Ltd.) were added to 100 parts by mass of an addition reaction type silicone rubber coating agent (trade name: SILMARK™, produced by Shin-Etsu Chemical Co., Ltd.) to produce a solution in which the proportion of the silicone resin fine particles to the coating film was 60% by mass.

Note that although SILMARK™ was used as the silicone rubber coating agent in the above-mentioned Examples 1 and 2, the present invention is not limited thereto, but it is also possible to use an addition reaction type coating agent such as trade names: KE-1844, KE-1846, KE-1886, KE-1871 (all thereof produced by Shin-Etsu Chemical Co., Ltd.), or the like. As the solvent for adjusting the viscosity, aromatic hydrocarbon based solvents such as benzene, toluene and xylene, aliphatic hydrocarbon based solvents such as n-hexane, n-heptane, n-octane, isooctane, nonan, decane, undecane, and dodecane, and the like can be used alone or in combination of two or more.

Subsequently, cables of the reference examples 1 to 3 were produced by changing the materials of the coating film. The process of forming the coating film over the surface of the sheath is the same as in Examples 1 and 2 above.

In the reference example 1, as the silicone rubber coating material, a solution was produced by adding to 100 parts by mass of a condensation reaction type silicone rubber coating agent (trade name: X-93-1755-1, produced by Shin-Etsu Chemical Co., Ltd.) containing vinyl oxime silane, toluene and n-heptane, 13 parts by mass of silicone resin fine particles having an average particle diameter of 2 µm (trade name: KIM-590, available from Shin-Etsu Chemical Co., Ltd.), and in which the proportion of the silicone resin fine particles to the coating film was 563% by mass. Using this solution, coating was carried out under the same conditions as in Example 1, followed by drying and curing treatment at a temperature of 120 degrees C. for 30 minutes. The film thickness of the produced silicone rubber coating film was about 15 μm. Note that the content of the silicone resin fine particles in the coating film was calculated assuming that the solid content (nonvolatile content) of the coating agent was 12% (data value of Shin-Etsu Chemical Co., Ltd.).

In the reference example 2, the conditions were the same as those in the Examples 1 and 2, except the use of a solution produced by adding to 20 parts by mass of silicone resin fine particles having an average particle diameter of 2 μm (trade name: KMP-590, available from Shin-Etsu Chemical Co., Ltd.), and in which the proportion of the silicone resin fine particles to the coating film was 16.7% by mass. The film thickness of the produced silicone rubber coating film was about 15 μm.

In the reference example 2, the conditions were the same as those in the Examples 1 and 2, except the use of a solution produced by adding to 200 parts by mass of silicone resin fine particles having an average particle diameter of 2 μm (trade name: KMP-590, available from Shin-Etsu Chemical Co., Ltd.), and in which the proportion of the silicone resin fine particles to the coating film was 66.6% by mass. The film thickness of the produced silicone rubber coating film was about 20 μm.

In the present embodiment, by adopting the above-described feature points, the configuration is realized in which the adhesion strength between the sheath and the coating film is 0.30 MPa or more. In the following description, experimental results supporting the fact that with this configuration, it is possible to prevent the peeling at the interface between the sheath and the coating film and the boot from coming off the probe cable will be described.

Figure 7:
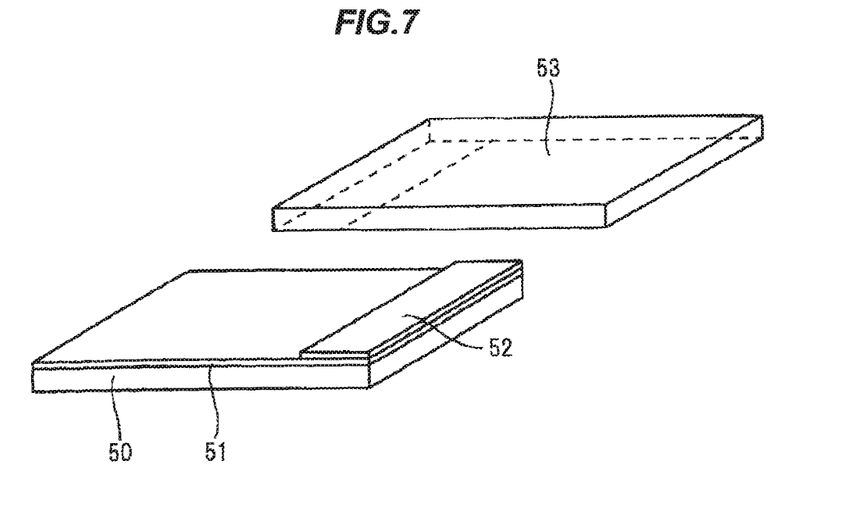
FIG. 7 is a diagram for explaining a method of producing an evaluation sample for evaluating the adhesion strength between the sheath and the coating film.
Figure 8:
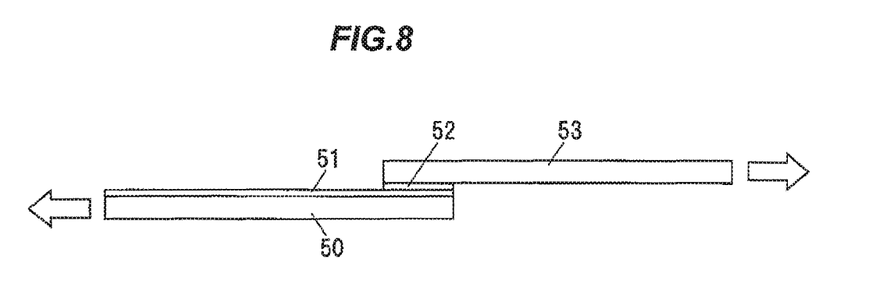
FIG. 8 is a schematic diagram showing a measuring method for measuring the tensile shear strength using the sample for evaluation.

First, the adhesion strength between the sheath and the coating film is substituted by the following measuring method. FIG. 7 is a diagram for explaining a method of producing an evaluation sample for evaluating the adhesion strength between the sheath and the coating film. In FIG. 7, a coating film 51 was formed over a surface of a sheath material sheet 50 having a thickness of the order of 1 mm and a width of the order of 25 mm, and a boot material sheet 53 having a thickness of the order of 1 mm and a width of the order of 25 mm was bonded to the surface of the coating film 51 with an adhesive 52. Note that the same silicone rubber (static friction coefficient: 1.0 or more) used for the sheath material sheet 50 and the boot material sheet 53. As the adhesive 52, a commercially available silicone based adhesive KE-45 (produced by Shin-Etsu Chemical Co., Ltd.) was used. The bonding area at this time was, e.g., 10 mm×25 mm, and the thickness of the adhesive material 52 was of the order of 50 μm to 200 μm. The sample for evaluation produced in this manner was left in the atmosphere at 25 degrees C. for 168 hours. Thereafter, the tensile shear strength is measured using the sample for evaluation to evaluate the adhesion strength between the sheath material sheet 50 and the coating film. FIG. 8 is a schematic diagram showing a measuring method for measuring tensile shear strength using the sample for evaluation. Specifically, as shown in FIG. 8, while holding the respective end portions of the sheath material sheet 50 and the boot material sheet 53, the sheath material sheet 50 and the boot material sheet 53 were pulled at a speed of 500 mm/min, and the tensile shear strength was measured to evaluate the adhesion strength between the sheath material sheet 50 and the coating film.

Figure 9:
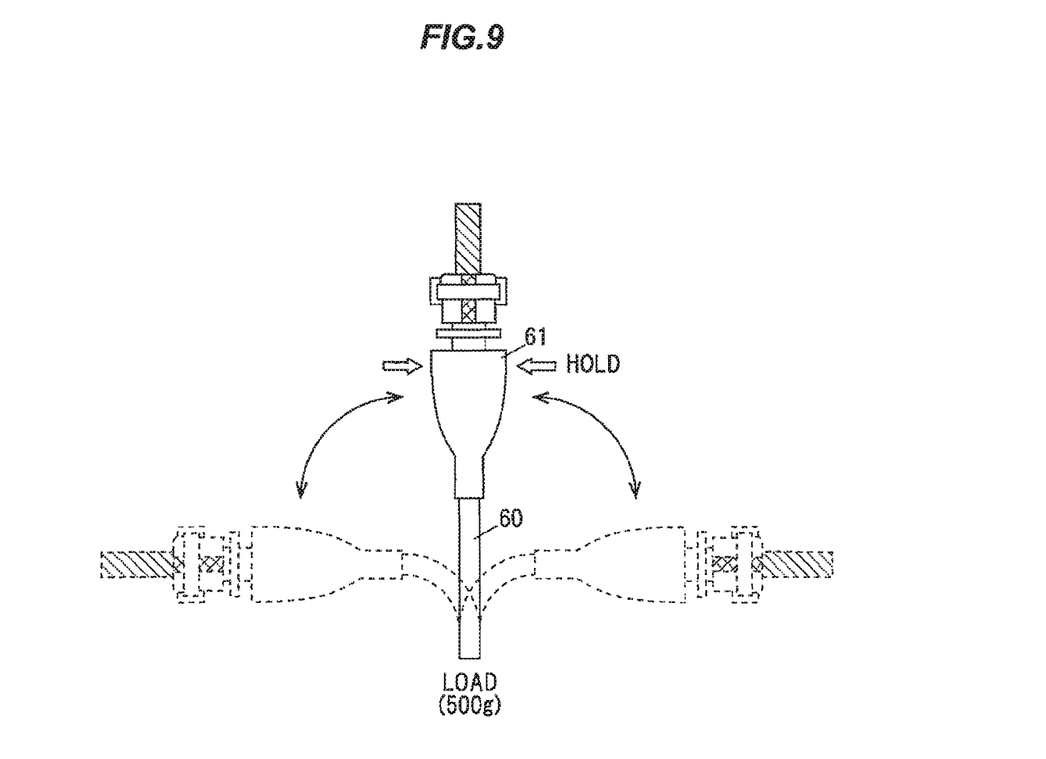
FIG. 9 is a schematic diagram showing a bending resistance test of a probe cable.

Next, a bending resistance test for examining bending resistance will be described. FIG. 9 is a schematic diagram showing a bending resistance test of a probe cable. In FIG. 9, in the bending resistance test, a load of 500 g was applied to the probe cable 60, and the probe cable 60 was held in a vertical state. The portion of a boot 61 attached to an end portion of the probe cable 60 is held, and the operations of bending this held portion to the right and left by 90 degrees at a speed of 30 times/min are performed. Here, the held portion is held in the vertical state, then bent to the left by 90 degrees, returned to be in the vertical state, then bent to the right by 90 degrees, and returned to be in the vertical state. The number of bendings was 150,000 times or more in total of right and left bendings. In such a bending resistance test, when no peeling or breaking of the boot 61 occurred, it was determined that the bending resistance was good (○). On the other hand, when the boot 61 peeled off or broke, the bending resistance was determined as poor (×).

Further, as to the "tackiness" of the surface, the static friction coefficient of the surface of the coating film was smaller than the static friction coefficient of the surface of the sheath, more concretely, when the static friction coefficient of the surface of the coating film was 0.5 or less, it was determined as "no tackiness" (○). On the other hand, when the static friction coefficient of the surface of the coating film was more than 0.5, it was determined as "tackiness" (×). The static friction coefficient was measured as follows. First, a test sheet 1 having a planar sheet coated with a material to be measured and having a length of about 10 cm and a width of about 2.5 cm mounted to a flat plate, and a sheet 2 having a 1.5 cm×1.5 cm square planar sheet mounted to a flat plate were prepared. The surface coated with the sheet 2 was brought from above into contact with the surface coated with the sheet 1 or the surface after the wiping in such a manner that they faced each other, and while a load W of 2 N was applied from above the sheet 2 flat plate, the flat plate with the sheet 2 was pulled horizontally with a push-pull gauge, and its pulling force (frictional force) F was measured. The static friction coefficient μ was calculated from F=μW.

The measurement results of the adhesion strengths between the sheath and the coating film, the bending resistances, and the static friction coefficients of Examples 1 and 2 and Reference Examples 1 to 3 were shown in Table 1.

TABLE 1

| | | | | | (Parts by mass if there is no description of unit) | | |
| | Items | Composition | Example 1 | Example 2 | Reference Example 1 | Reference Example 2 | Reference Example 3 |
| --- | --- | --- | --- | --- | --- | --- | --- |
| | Sheath | Silicone rubber[1] | 100 | 100 | 100 | 100 | 100 |
| Coating film | Parent material | Addition reaction type silicone rubber | 100 | 100 | | 100 | 100 |

TABLE 1-continued

| Items | Composition | Example 1 | Example 2 | Reference Example 1 | Reference Example 2 | Reference Example 3 |
|---|---|---|---|---|---|---|
| | coating agent[2] Condensation reaction type silicone rubber coating agent[3] | | | 100 | | |
| Fine particles | Silicone resin fine particles[4] | 120 | 150 | 13 | 20 | 200 |
| Viscosity adjustment solvent | Toluene | 600 | 600 | | 600 | 600 |
| Curing inhibitor[5] | | 8 | 8 | | 8 | 8 |
| Curing catalyst[6] | | 0.3 | 0.3 | | 0.3 | 0.3 |
| Coating film thickness (μm) | | About 17 | About 18 | About 15 | About 15 | About 20 |
| Fine particles/ coating film ratio (mass %) | | 54.5 | 60.0 | 56.5 | 16.7 | 66.6 |
| Static friction coefficient of sheath (μ) | | 1.0 or more | 1.0 or more | 1.0 or more | 1.0 or more | 1.0 or more |
| Static friction coefficient of coating film surface (μ) | | 0.16 | 0.14 | 0.16 | 1.0 | 0.13 |
| Adhesion strength between sheath and coating film (MPa) | | 0.36 | 0.30 | 0.25 | 0.40 | 0.20 |
| Surface tackiness | | ○ | ○ | ○ | × | ○ |
| Bending resistance | | ○ | ○ | × | ○ | × |

[1] Product Name: KE-541-U (static friction coefficient: 1.0 or more), manufactured by Shin-Etsu Chemical Co., Ltd.
[2] Product Name: SILMARK-TM, manufactured by Shin-Etsu Chemical Co., Ltd.
[3] Product Name: X-93-1755-1, manufactured by Shin-Etsu Chemical Co., Ltd.
[4] Product Name: KMP-590 (average particle size: 2 μm), manufactured by Shin-Etsu Chemical Co., Ltd.
[5] Product Name: CAT-TM, manufactured by Shin-Etsu Chemical Co., Ltd.
[6] Product Name: CAT-PL-2, manufactured by Shin-Etsu Chemical Co., Ltd.

Table 1 shows that, in the reference example 2 in which the fine particles/coating film ratio is 16.7 mass %, the bending resistance was good (○) but the static friction coefficient of the coating film surface was 1.0 which is substantially equal to the static friction coefficient of the sheath surface, and the "tackiness" remained on the coating film surface.

In Example 1 in which the adhesion strength between the sheath and the coating film was 0.36 MPa, the bending resistance was good (○). Similarly, also in Example 2 in which the adhesion strength between the sheath and the coating film was 0.3 MPa, the bending resistance was good (○). On the other hand, in the reference example 1 in which the adhesion strength between the sheath and the coating film is 0.25 MPa, the bending resistance was poor (×).

In the reference example 3 in which the fine particles/ coating film ratio is 66.6 mass %, although the static friction coefficient of the coating film surface was low, the adhesion strength between the sheath and the coating film was 0.20 MPa which is low, and the bending resistance was poor (×).

Based on the above experimental results, it is found that the fact that according to the constitution in which the adhesion strength between the sheath and the coating film is 0.30 MPa or more, it is possible to prevent the peeling at the interface between the sheath and the coating film and the boot from coming off the probe cable, is supported.

Regarding the coating agent (parent material) of the coating film, as described above, in the case of the condensation reaction type, when the silicone rubber is solidified from the liquefied silicone rubber, the gas escapes from the silicone rubber, whereby voids are formed in the solidified silicone rubber. On the other hand, in the case of the addition reaction type, bubbles are hardly formed in the coating film. Therefore, in Examples 1 and 2 using the addition reaction type coating agent, it is considered that bubbles in the coating film were lessened at the interface with the sheath, and the high adhesion strength was able to be obtained. Note that in Examples 1 and 2, an adhesion strength of 0.30 MPa or more was obtained without adding an adhesion improver such as a silane coupling agent. On the other hand, in the reference example 1 in which the adhesion was low, an adhesion improver was further added, but no improvement in adhesion was observed.

In the above embodiment, the probe cable connectable to the medical device has been described as an example. However, the technical idea in the above embodiment is not limited to this, but can be widely applied to various types of cables that require bending resistance, for example.

For example, it is suitable for cables for applications in which the friction between cables such as medical cables (endoscope cables, catheter connection cables, etc.) other than probe cables and cabtire cables or the like or between them and a contact object is a problem. Further, the cable core (electric wire) constituting the cable is not limited to the coaxial wire (coaxial cable), but may be, for example, an electric wire in which an insulator is coated around the outer circumference of a conductor made of a single wire or a stranded wire such as a pure copper wire or a tin-plated copper wire, or an optical fiber or the like.

Further, the sheath 20 is not limited to silicone rubber, but is not particularly limited as long as it can be used as the sheath material. For example, polyethylene, chlorinated polyethylene, chloroprene rubber are preferred. Further, since it is expected that the discoloration due to the UV light may be suppressed to some extent by providing the coating film 23, it is also possible to use the polyvinyl chloride as the sheath 20. In particular, the present invention is highly applicable when the sheath is composed of a material with low slidability, that is, a material with high frictional force or a material with high tackiness. Representative examples are rubber compositions such as silicone rubber and chloroprene rubber with adhesiveness (stickiness) having a static friction coefficient μ of 0.7 or more when used as a sheet base material. The above materials can be used not only alone but also as a composition containing two or more kinds.

To the composition serving as time sheath material, general compounding agents such as various crosslinking agents, crosslinking catalysts, antioxidants, plasticizers, lubricants, fillers, flame retardants, stabilizers, colorants and the like may be added. The sheath can be provided by extrusion coating film and, if necessary, crosslinked. The sheath can also be of a multilayer structure. In this case, when the outermost layer of the multilayer structure is composed of the above-mentioned materials, the present invention is highly applicable.

Further, the present invention is also applicable to a medical hollow tube such as a catheter.

Figure 10A:
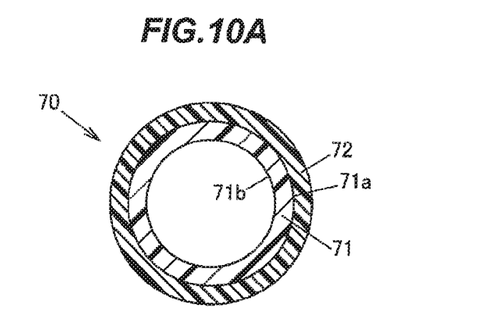
FIG. 10A is a cross sectional view of a hollow tube for medical use including a hollow tube body and an outer coating film on an outer surface of the hollow tube body.
Figure 10B:
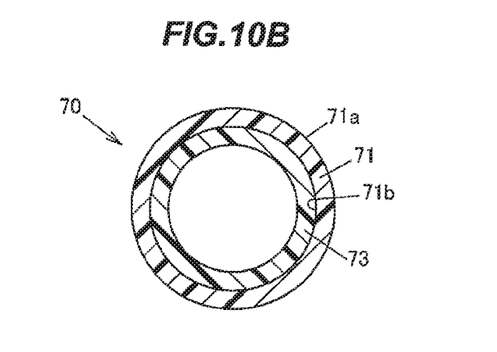
FIG. 10B is a cross sectional view of a hollow tube for medical use including a hollow tube body and an inner coating film on an inner surface of the hollow tube body.
Figure 10C:
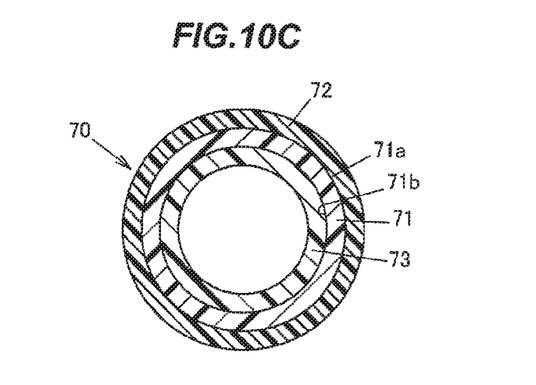
FIG. 10C is a cross sectional view of a hollow tube for medical use including a hollow tube body, an outer coating film on an outer surface of the hollow tube body and an inner coating film on an inner surface of the hollow tube body respectively.

FIG. 10A is a cross sectional view of a hollow tube 70 for medical use including a hollow tube body 71 and an outer coating film 72 on an outer surface 71a of the hollow tube body. FIG. 10B is a cross sectional view of a hollow tube 70 for medical use including a hollow tube body 71 and an inner coating film 73 on an inner surface 71b of the hollow tube body 71. FIG. 10C is a cross sectional view of a hollow tube 70 for medical use including a hollow tube body 71, an outer coating film 72 on an outer surface 71a of the hollow tube body 71 and an inner coating film 73 on an inner surface 71b of the hollow tube body 71, respectively.

That is, in a hollow tube 70 for medical use comprising a hollow tube body 71 (made of e.g., silicone rubber), and an outer coating film 72 and/or an inner coating film 73 covering the circumference (an outer surface 71a or an inner surface 71b, or both surfaces) of the hollow tube body 71 and adhering to the hollow tube body 71, the coating film 23 of the embodiment described above can be used as the outer coating film 72 and/or the inner coating film 73, and static friction coefficient of the surface of the outer coating film 72 and/or the inner coating film 73 is smaller than static friction coefficient of the surfaces of the hollow tube body 71, and the adhesion strength between the hollow tube body 71 and the coating film 72 and/or the inner coating film 73 is 0.30 MPa or more. With such a medical hollow tube, since there is no "tackiness" on the inner surface or outer surface of the hollow tube 70, when an instrument is used by being inserted into the medical hollow tube such as a catheter for example, it is possible to smoothly insert and remove the instrument.

Although the invention made by the present inventors has been concretely described based on its embodiments, the present invention is not limited to the above-mentioned embodiment, and it goes without saying that various modifications can be made without departing from the spirit thereof.

Although the invention has been described with respect to the specific embodiments for complete and clear disclosure, the appended claims are not to be thus limited but are to be construed as embodying all modifications and alternative constructions that may occur to one skilled in the art which fairly fall within the basic teaching herein set forth.

What is claimed is:

1. A cable, comprising:
   a sheath; and
   a coating film covering a circumference of the sheath, the coating film adhering to the sheath,
   wherein a static friction coefficient of a surface of the coating film is 0.5 or less,
   wherein an adhesion strength between the sheath and the coating film is 0.30 MPa or more, and
   wherein a parent material of the coating film is produced by curing an addition reaction type coating agent.

2. The cable according to claim 1, wherein the coating film comprises fine particles dispersed in a parent material.

3. The cable according to claim 2, wherein the fine particles include any one or a plurality of silicone resin fine particles, silicone rubber fine particles, or silica fine particles.

4. The cable according to claim 2, wherein the fine particles have a higher hardness than that of the parent material.

5. The cable according to claim 2, wherein the fine particles comprise an average particle diameter of 1 μm or more and 10 μm or less.

6. The cable according to claim 1, wherein the coating film comprises a thickness of 3 μm or more and 100 μm or less.

7. The cable according to claim 1, wherein the sheath is made of silicone rubber.

8. The cable according to claim 1, wherein the cable is a probe cable, which is connectable to a medical device.

9. The cable according to claim 1, wherein a roughness of an uneven shape of the surface of the coating film is higher than a roughness of an uneven shape of the surface of the sheath.

10. The cable according to claim 1, further comprising:
    a protective member bonded around the coating film,
    wherein a static friction coefficient of a surface of the coating film is smaller than a static friction coefficient of a surface of the sheath, and
    wherein an adhesion strength between the sheath and the coating film is equal to a bonding strength between the coating film and the protective member, or greater than the bonding strength between the coating film and the protective member.

11. The cable according to claim 1, wherein the coating film is an addition reaction type silicone rubber.

12. The cable according to claim 11, wherein the coating film is substantially void-free in an interface between the coating film and the sheath.

* * * * *